United States Patent [19]
Coleman et al.

[11] Patent Number: 5,233,996
[45] Date of Patent: Aug. 10, 1993

[54] PATIENT INTERFACING SYSTEM AND METHOD TO PREVENT WATER CONTAMINATION

[75] Inventors: Dennis L. Coleman, Salt Lake City; Charles V. Owen, Highland; Noel de Nevers, Salt Lake City, all of Utah

[73] Assignee: BOC Health Care, Inc., New Providence, N.J.

[21] Appl. No.: 647,170

[22] Filed: Jan. 24, 1991

Related U.S. Application Data

[63] Continuation of Ser. No. 559,502, Jul. 23, 1990, abandoned, which is a continuation of Ser. No. 196,725, May 20, 1988, abandoned.

[51] Int. Cl.⁵ .......................... A61B 5/08; A67B 7/105
[52] U.S. Cl. ..................................... 128/716; 128/719; 128/205.27; 128/205.29
[58] Field of Search .............. 128/208.26, 203.24, 128/204.17, 205.1, 12, 205.22–205.29, 716, 719, 728; 73/863.12, 23.37, 29.01

[56] References Cited

U.S. PATENT DOCUMENTS

| | | | |
|---|---|---|---|
| 3,507,146 | 4/1970 | Webb | 128/719 |
| 3,649,199 | 3/1972 | Littlejohn | |
| 3,735,558 | 5/1973 | Skarstrom et al. | |
| 4,060,074 | 11/1977 | Russo | |
| 4,090,513 | 5/1978 | Togawa | |
| 4,167,667 | 9/1979 | Hall et al. | |
| 4,297,871 | 11/1981 | Wright et al. | |
| 4,425,804 | 1/1984 | Moint et al. | 128/725 |
| 4,485,822 | 12/1984 | O'Connor et al. | |
| 4,549,553 | 10/1985 | Hochberg | |
| 4,572,208 | 2/1986 | Cutler et al. | |
| 4,705,543 | 11/1987 | Kertzman | |
| 4,727,871 | 3/1988 | Smargiassi et al. | 128/201.17 |
| 4,729,700 | 2/1988 | Jaasma | 73/29.01 |
| 4,799,374 | 1/1989 | Bossart et al. | 128/719 |
| 4,808,201 | 2/1989 | Kertzman | |
| 4,958,075 | 9/1990 | Mace et al. | 128/719 |
| 5,012,052 | 4/1991 | Hayes | 73/23.37 |
| 5,042,500 | 8/1991 | Norlen et al. | 128/719 |
| 5,072,737 | 12/1991 | Gouldins | 128/205.23 |

OTHER PUBLICATIONS

Auchincloss, Jr. et al., "Control of water vapor during rapid analysis of respiratory gases in expired air", Journal of Applied Physiology, vol. 28, No. 2, Feb. 1970, pp. 245–247.

Scheid et al., "Electronic compensation of the effects of water vapor in respiratory mass spectrometry", Journal of Applied Physiology, vol. 30, No. 2, Feb. 1971, pp. 258–259.

Deno et al., "A dryer for rapid response on-line expired gas measurements", Journal of Applied Physiology: Respirat. Environ. Exercise Physio., vol. 46, No. 6, 1979, pp. 1196–1199.

Wong et al., "Eliminating the Effect of Water Vapor in Respiratory Gas Analysis", Journal of Clinical Engineering, vol. 7, No. 2, Apr.-Jun. 1982, pp. 159–166.

Walter Grot, "Discovery and development of Nafion perfluorinated membranes", Chemistry and Industry, Oct. 7, 1985, pp. 647–649.

*Primary Examiner*—Randall L. Green
*Assistant Examiner*—R. Reichle
*Attorney, Agent, or Firm*—Dennis H. Epperson; Roger M. Rathbun; Larry R. Cassett

[57] ABSTRACT

Described herein is a patient interfacing system for sampling the inspired and expired gases of a patient and removing moisture from the sample. In one embodiment of the present invention, a patient link receives the gases from the patient's airway circuit and a vaporization section vaporizes condensed moisture in the sample. A separator section allows the vaporized moisture component of the sample to exit the patient interfacing system before the gas sample reaches the monitoring instrument. A filter may also be utilized to prevent condensed moisture, particulates and liquids from entering the monitoring instrument. Thus, the patient interfacing system of the present invention provides a reliable, cost effective and efficient means for delivering gas samples to a monitoring instrument which reduces or prevents water condensation inside the gas analysis portion of the monitoring instrument.

8 Claims, 2 Drawing Sheets

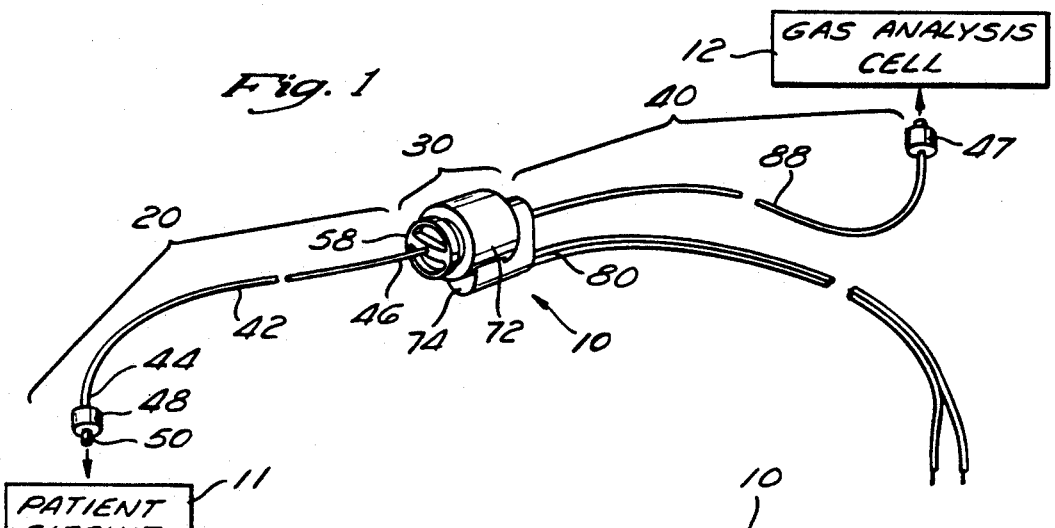
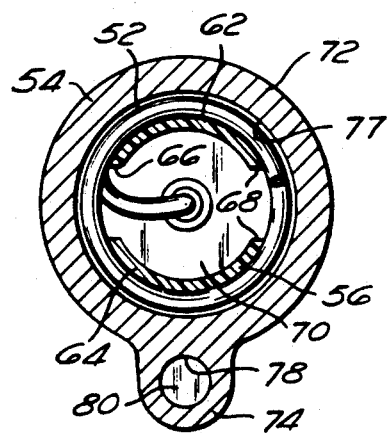
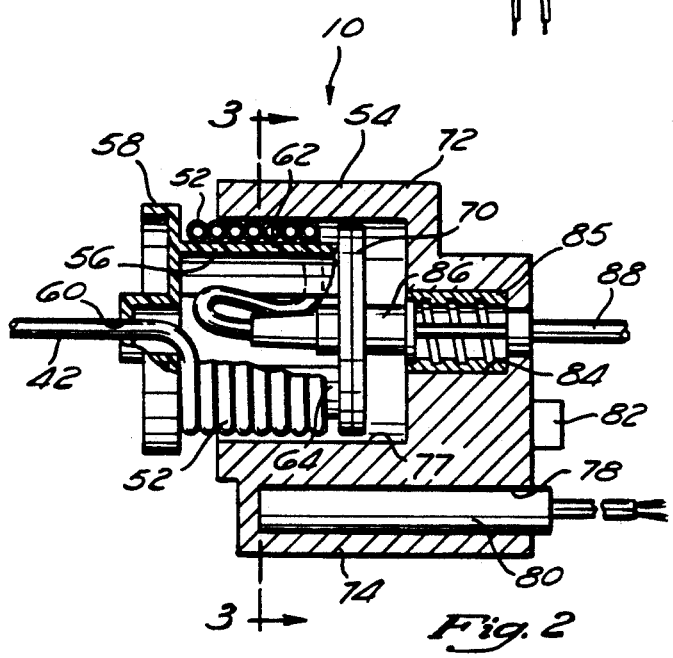
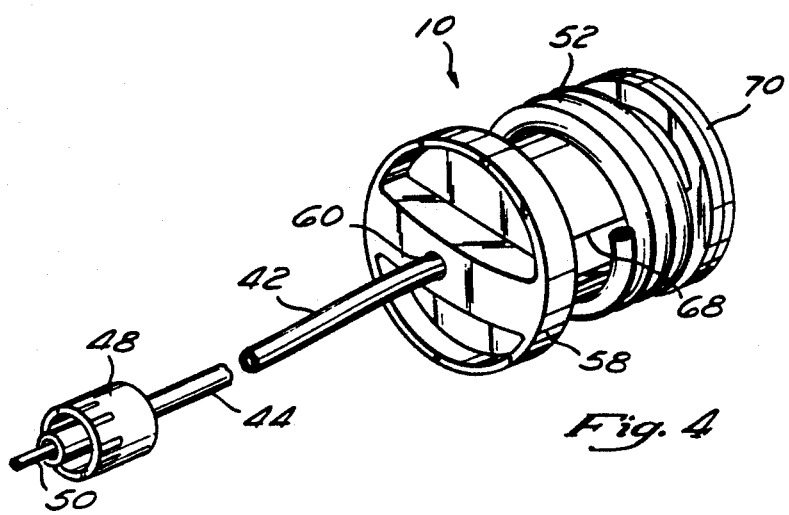

PATIENT INTERFACING SYSTEM AND METHOD TO PREVENT WATER CONTAMINATION

This application is a continuation of application Ser. No. 559,502, filed Jul. 23, 1990, which itself is a continuation of application Ser. No. 196,725, filed May 20, 1988, both of which applications are now abandoned.

FIELD OF THE INVENTION

This invention relates to a system and method of interfacing a patient with monitoring equipment that monitors inspired and expired gases, and more particularly, to a system and method for preventing condensed water or other liquids from entering the detection portion of the monitoring equipment.

BACKGROUND OF THE INVENTION

Respiratory and anesthetic gas monitoring has achieved a high standard of technological advancement with the development of monitoring techniques that enable quick diagnosis and treatment of unfavorable trends in the condition of a patient, improved survival rates, early extubation following surgery and shorter times in intensive care units. Applications of respiratory gas and anesthetic agent monitoring include the measurement of oxygen consumption, carbon dioxide production, anesthetic agent uptake and the detection of anesthesia machine circuit disconnections and introduction of air emboli into the blood. Continuous analysis of patients' respiratory and anesthetic gases is becoming increasingly important in improving patient safety during the course of treatment. For example, breath-by-breath monitoring of the concentrations and identity of the anesthetic agents present in a patient's respiratory gases leads to a more scientific basis for the administration and control of the anesthetic agents.

Continuous, breath-by-breath monitoring of a patient's respiratory gases and simultaneous determination of multiple specific respiratory gases and anesthetic agents in the patient's system can often facilitate diagnosis and treatment, anticipate and prevent the development of oncoming problems, and otherwise provide instant data for physicians and other health care personnel to use in therapeutic situations. Measurements of any gas of interest in a patient's breath can be sampled on a continuous basis and monitored by an appropriate type of gas analyzer. For example, when monitoring a patient's carbon dioxide level, a sharp reduction of carbon dioxide in the breath might indicate an imminent failure of respiration. Similarly a sharp increase in the level of carbon dioxide might be an indication of other conditions requiring attention.

Respiration monitoring of patients is now available utilizing many types of commercially available gas analyzers including infrared (IR), polaragraph, mass spectrometer (MS), Raman spectrometer, etc. Due to the high cost of some of the monitoring equipment, a single monitor may be connected to several patients simultaneously. In many of these situations, the gas analyzer is placed in a remote location and lengthy capillary tubes are used to connect the patients to the analyzer unit. Since it is common practice to humidify inspired gas, and since the expired gas from the patient is often at nearly 100% relative humidity and 37 degrees centigrade, water can easily condense at room temperature in the tubing interfacing the patient with the analyzer. Virtually all commercially available gas analyzers (e.g., IR, polaragraph, MS, Raman spectrometer, etc.) are adversely affected if condensed water or other liquids enter the detector portion of the analyzer. Additionally, the presence of water vapor in samples of expired gas can be a source of error when making measurements of expired gas concentrations.

One prior method for removing water vapor from expired gases prior to analysis physically drys the expired gas, for example, by introducing the expired gas into a desiccator. One such system has been developed using a desiccator filled with calcium sulfate ($CaSO_4$) as the drying agent. Such desiccator systems experience at least two significant problems. First, the drying agent must be carefully monitored and replaced on a regular basis when it is depleted. Second, the large desiccator volume required to perform the drying of the gas makes for increased dead space within the system and thus results in longer "washout times" for measuring changes in gaseous composition. The term dead space refers to any space in the system between the point where the sample is tapped from the patient and the point at which the sample enters the gas analyzer. This would include the space within the connecting tubes, filters, desiccants, valves, traps etc. The term "washout time" refers to the amount of time which is needed for a unit of gaseous sample to wash out or displace the gas already within the system.

Washout time is an important factor in monitoring changes in the concentrations of oxygen, carbon dioxide, anesthetic agents and other constituents of the patient's inspired and expired gases. Where large total volumes or dead volumes are present within a metabolic gas monitoring system, corresponding large washout times are created, resulting in decreased ability to quickly and accurately measure time dependent changes in the composition of the inspired and expired gases. The long washout times associated with desiccator systems do not allow for the dynamic response necessary to measure time dependent changes in the oxygen and carbon dioxide concentrations in breath-by-breath analysis of expired gas. The large total volumes and dead volumes of desiccator systems have resulted in less sensitivity to changes in the composition of the gases analyzed and less accurate measurements of the oxygen, carbon dioxide and anesthetic agent components of the gases. Thus, systems which use drying agents to remove the water vapor often require frequent replacement of the drying agent and often introduce long delay times in the sampling line precluding the acquisition of breath-by-breath data. Additionally, in some applications, the drying agent may absorb the gas being monitored and lead to inaccurate measurements.

Another common technique for removing moisture, patient secretions and other liquids from gas samples employs cold traps in the gas line to condense the moisture. Condensation techniques have generally not been completely successful due in part to the excessively large dead spaces which are added to the gas transport system by the cold traps. The large dead space and long washout time problems previously described with respect to desiccator systems also apply to cold trap systems.

One such cold trap system is described in the article entitled "A DRYER FOR RAPID RESPONSE ON-LINE EXPIRED GAS MEASUREMENTS" by N. S. Deno and E. Kamon. This article discloses a water condensation method for drying an expired gas sample before it reaches an analyzer. The disclosed method utilizes a dryer which consists of an ice bath condenser and a separator for removing the condensed water. As with other cold trap condenser devices, this approach has long response times which reduce the utility of the device for breath-by-breath analysis measurements.

The article entitled "ELIMINATING THE EFFECT OF WATER VAPOR IN RESPIRATORY GAS ANALYSIS" by Larry G. Wong and Dwayne R. Westenskow reports a method for partially eliminating water vapor from expired air samples by cooling the gas samples to a known temperature. This technique substantially minimizes the effects of water vapor pressure on $O_2$ measurements. Based on Dalton's law of partial pressures, the vapor pressure of water at a given temperature and pressure is constant and is independent of other gas concentrations. The effects of water vapor in expired gas analysis are reduced by bringing all sampled gases to a specific lowered temperature. By reducing the temperature of the saturated gas sample to a known temperature, the water vapor partial pressure may be determined. Thus, when gases are sufficiently equilibrated with temperature in an appropriate apparatus, water vapor pressure is constant. However, the above-described system is not suited for breath-by-breath measurements because large dead spaces degrade several desired performance characteristics including response time. Furthermore, this system, while removing a small quantity of moisture from the sample, is not primarily a water removal system and allows most of the water vapor contained in the gas sample to enter the gas analyzer.

U.S. Pat. No. 4,090,513 entitled "HEAT AND MOISTURE EXCHANGING DEVICE FOR RESPIRATION" discloses a device for removing moisture from a tube carrying respiratory air. The moisture accumulates on an exchange layer and flows out of the device through a drainage tube. As with other condensation moisture removal systems, decreased response time and water removal considerations limit the applications for which this system is suitable.

Another approach for preventing liquids from reaching a monitoring device is disclosed in U.S. Pat. No. 4,485,822 entitled "MULTI-PHASE INTERFACING SYSTEM AND METHOD". This patent discloses a patient interface which relies on a disc-shaped hydrophobic filter to prevent fluids from entering the analyzer. This system overcomes the poor response time of most cold trap and desiccator systems by using a low dead space volume disc filter. In such an interface, however, in the event that the patient requires a humidifier, enough water can condense within the filter to occlude gas flow through the filter. In some cases, this can occur within 30 minutes, depending on the gas flow rate to the analyzer and the ambient temperature. Not only is this inconvenient for the medical staff and patient, since the filter must be changed frequently, but this can also result in a loss of vital medical information during the time period that the filter is being changed.

U.S. Pat. No. 4,549,553 entitled "APPARATUS AND METHOD FOR USE IN A MEDICAL GAS SAMPLING SYSTEM", discloses an approach for providing a sample gas flow from an air tube to a patient undergoing automatic ventilation. The air tube includes a gas diffusive membrane disposed in a wall of the air tube. The gas diffusive membrane may be made of water absorbing or water passing materials to eliminate excess water from accumulating and blocking the gas sample flow. In a preferred embodiment a non-wettable gas diffusive membrane is used to prevent or reduce water from entering the sample gas flow; otherwise, water saturates the membrane and water eventually passes through the membrane to enter the gas sample flow. By non-wettable it is meant that the membrane resists or cannot be saturated with liquid and its surfaces resist or cannot be covered with liquid. A Teflon ® mesh membrane is a suitable non-wettable membrane for this application. Teflon ® is a registered trademark of E. I. Du Pont de Nemours & Company, Inc in Wilmington, Del. This approach, while perhaps reducing the frequency of sample flow blockage, does nothing to remove the moisture from the system and is still susceptible to occlusion in long term usage. Additionally, the embodiment shown in FIG. 1A incorporates a large volume funnel 20 which increases the dead space volume in the gas transport system and results in poor response time characteristics.

A more recent approach for preventing water from condensing in the gas transport circuitry uses interface tubing comprising a polymer that is highly permeable to water vapor, but simultaneously has a very low permeability for the respiratory and anesthetic gases being analyzed. One such polymer was developed by Du Pont scientists and is marketed in tubing form as Nafion ® tubing. Nafion ® is a registered trademark of E. I. Du Pont de Nemours & Company, Inc. in Wilmington, Del. By attaching the Nafion ® tubing directly to the patient breathing circuit near the connection to the patient, a majority of the water vapor in the sample gases diffuses out before it arrives at the filter barrier. The disadvantage of this approach is the high cost of the Nafion ® tubing. A section of Nafion ® tubing of sufficient length to remove the desired amount of water vapor is very expensive in relation to the cost of the other components comprising the patient interface. Therefore, it is generally considered a reusable rather than a disposable gas sampling line and, as such, requires cleaning and sterilization between uses.

Many of the attempts heretofore to remove liquids from patient interfaces introduce levels of dead space into the interfacing system which adversely affect the accuracy of the results produced by the monitoring system. Other attempts which overcome the dead space problems either 1) utilize expensive materials which, when incorporated into a disposable patient interface, make the interface very expensive for a one time use item, or 2) are subject to blockage in short periods of time.

The proliferation of respiratory gas monitoring techniques and the increased demand for breath-by-breath respiratory gas monitoring accentuate the need for a patient interfacing system which prevents moisture from reaching the detection portion of the gas analysis systems. Such a patient interface system should reduce or eliminate the frequency of occlusion or contamination of the gas transport system and detection portion of the gas analyzer. This system should eliminate or reduce the risk of water vapor condensing within and clogging components of the system such as the inline filter or the analyzer gas cell. In addition, the patient interface system will desirably provide a barrier to prevent contamination in the form of secretions, condensed water, and particulates from entering the gas analyzer. It is preferred that such an interfacing device be a one time use item for hygienic reasons. However, for economic reasons, a one time use item must also not be prohibitively expensive if is to be disposed of after a single use. The device of the present invention satisfies all of these requirements.

SUMMARY OF THE INVENTION

The present invention is a method and apparatus for interfacing a patient with gas analysis equipment that monitors inspired and expired gases of a patient. The invention utilizes a vaporization technique to inhibit or prevent moisture contained in the inspired and expired gases from obstructing the sample line or from reaching the detector portion of the gas analyzer.

More specifically, the invention relates to a method and system for interfacing a patient with a gas monitoring apparatus for analysis of a patient's respiratory gases. One embodiment of the invention includes a patient link which receives a sample of exhaled gases from the patient's airway. The patient link comprises a tubing section which is attached to a vaporization section. In a preferred embodiment, the vaporization section comprises a coil of tubing formed by wrapping the tubing around a cylindrical spool in a plurality of proximate turns. The vaporization section is encased by a heated element which advantageously facilitates the vaporization of any condensed moisture which is typically contained in the respiratory gases. Attached to the output of the vaporization section is a hydrophobic filter which is permeable to the vaporized moisture but inhibits the passage of particulates and liquids. After passing through the filter, the gases enter a separator section comprising a tubing material that is highly permeable to water vapor but has a very low permeability for respiratory gases, anesthetic agent gases and other gases being analyzed. The vaporized moisture which passes through the filter diffuses out of the system through the separator section of water vapor permeable tubing substantially reducing the amount of moisture which enters the detector portion of the gas analyzer.

In one embodiment of the invention the invention comprises an apparatus for sampling the respiratory gases of a patient through an airway circuit and delivering the gas sample to a gas analysis cell. A patient link comprising a first length of tubing connects to the airway circuit, receives the sample of respiratory gases and transports the sample toward the gas analysis cell. A vaporization section receives the sample from the patient link and vaporizes moisture contained in the sample. The vaporization section comprises a vaporization coil which comprises a spool having a cylindrical body portion. The body portion has a first end and a second end. A second length of tubing wraps around the body portion to form a coil having a plurality of proximate turns and a coil output. A disc-shaped filter having an input and an output is located at the second end of the cylindrical body wherein the input to the filter connects to the output from the coil. The vaporization section is surrounded by a heating block having a means for heating the block to a predetermined temperature and a chamber within the block for receiving the vaporization coil. A separator section having an input and an output is connected to the output of the disc filter, wherein the separator receives the gas sample from the filter and removes the water vapor portion from said gas sample to form a dried gas sample. The separator section then delivers the dried gas sample to the gas analysis cell.

In one embodiment, the separator section comprises a water vapor permeable section. For example, the water vapor permeable section may be a section of Nafion ® tubing.

Another embodiment of the invention comprises an apparatus for sampling gases in the airway of a patient and delivering the sample to a gas monitor wherein the apparatus comprises: a patient link for obtaining the gas sample from the patient airway and a vaporization section which receives the gas sample from the patient link and vaporizes condensed moisture contained in the sample before delivering the sample to the gas monitor.

The invention further comprises a method of monitoring patient gases comprising the steps of: 1) extracting a sample portion of the gases from the patient; 2) vaporizing moisture contained in the sample portion; 3) removing the vaporized moisture from the sample; and 4) delivering the sample to a monitoring apparatus.

The interfacing system of the present invention has several significant advantages over alternate systems and methods. It reduces filter occlusion as a result of condensed water by utilizing vaporization techniques. It eliminates or reduces the risk of water vapor condensing inside the analyzer and contaminating the gas analysis cell inside the instrument. Thus, the present invention overcomes many of the limitations of prior art devices in a device which offers superior performance in a cost effective manner.

BRIEF DESCRIPTION OF THE DRAWINGS

The preferred embodiment of the present invention is illustrated in and by the following drawings in which like reference numerals indicate like parts and in which:

FIG. 1 is a perspective view illustrating a patient interfacing system in accordance with the present invention.

FIG. 2 is a cross section view illustrating details of the vaporization section of the invention.

FIG. 3 is a cross section taken along the line 3—3 of FIG. 2.

FIG. 4 is a perspective view illustrating the patient link and vaporization coil of the invention.

DETAILED DESCRIPTION OF THE PREFERRED EMBODIMENT

Figure 5:
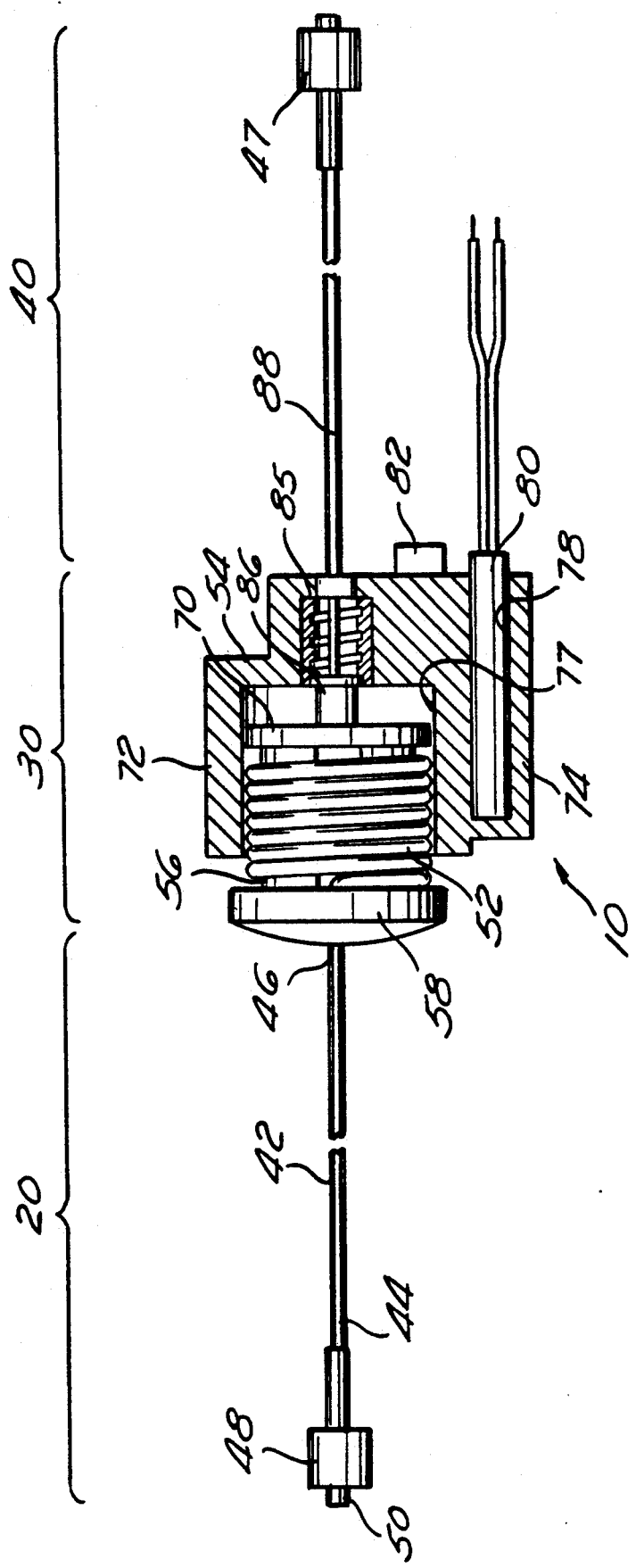
FIG. 5 is a plan view of the patient interfacing system of FIG. 1.

FIGS. 1, 4 and 5 show a patient interfacing system 10 which incorporates features of a preferred embodiment of the present invention. The interfacing system 10 is a device for connecting a patient via a patient circuit 11 with gas monitoring equipment 12 that samples and monitors inspired and expired gases of the patient. The patient interfacing system 10 may be used with most commercially available gas analyzers including but not limited to infrared (IR), polaragraph, mass spectrometer (MS), Raman spectrometer, etc. One specific gas analyzer with which the present invention is compatible is described in copending patent application Ser. No. 106,791 entitled "MULTI-CHANNEL MOLECULAR GAS ANALYSIS BY LASER ACTIVATED RAMAN LIGHT", assigned to the assignee of the present invention and hereby incorporated herein by reference.

The interface system 10, as shown in FIGS. 1 and 5, comprises a patient link 20, a vaporization section 30 and a separator section 40. The patient link 20 comprises a length of flexible tube or hose 42 having an input end 44 and an output end 46. The input end 44 is connected to the patient's airway passage and the output end 46 is connected to an input of the vaporization section 30. An output of the vaporization section 30 is connected to an input of the separator section 40 which has an output 47 connected to a gas input of the gas monitor 12.

In operation, the patient link 20 taps into the patient's airway passage and receives a sample of the patient's inspired and expired gases. The tubing 42 delivers the sample to the vaporization section 30. Since the gas sample may have a high moisture content, it is possible that some of the moisture will condense before it reaches the vaporization section 30. In accordance with one embodiment of the invention, the vaporization section 30 heats the gas sample to vaporize any condensed moisture contained in the sample. Thus, any condensed water which reaches the vaporization section is vaporized while passing through this section of the gas transport system. The air sample is then transported to the separator section where the water vapor portion of the sample is separated from the remaining gases comprising the sample. In this manner, only substantially dry gas samples are permitted to enter the gas analyzer. Typically, an air or vacuum pump, which is a component of the gas analyzer, pumps or draws air from the patient's airway through the interface system 10 into the gas analyzer.

The patient link 20 comprises a connector 48 at the input end 44. In one embodiment, the connector 48 has a tube 50 extending therefrom which enters a facial orifice of the patient and terminates within the patient's airway at a point from which the sample of respiratory or anesthetic gases is to be extracted. The connector 48 may be attached to an endotracheal conduit, a nasal cannula, or a facial mask device to facilitate entrance into the patient's airway via a tracheal incision, the nose and/or the mouth, respectively. A more detailed description of various means for entering the patient's airway may be found in U.S. Pat. No. 4,485,822.

The flexible tube 42 delivers the samples of the inspired and expired gases to the vaporization section 30 of the interface 10. The tubing 42 is preferably a cylindrical shape tubing made from a resilient and flexible material. It is preferable that the tubing have a small diameter to facilitate continuous and rapid transportation of samples of inspired and expired gases to the monitoring instrument. The small diameter reduces the dead space volume of the interface 10, which as explained previously, gives the system a fast response time which is particularly advantageous in breath-by-breath analysis procedures. It is preferable that the inside diameter (ID) of the tubing 42 be selected to be in the range of from approximately 0.020 inches to approximately 0.060 inches and the tubing wall thickness be in the range of from approximately 0.010 inches to approximately 0.040 inches. This range of tubing dimensions will facilitate a gas flow rate in the range of from approximately 30 ml/min to approximately 400 ml/min. In one embodiment, the ID of tubing section 42 is approximately 0.040 inches and the wall thickness is approximately 0.032 inches. In this embodiment, the length of the tubing section 42 included between the input end 44 and the output end 46 is approximately ten feet. It will be understood, however, that these dimensions are by way of example only and that other dimensions could be selected for practicing the present invention.

In one embodiment, the vaporization section 30 comprises a coil of flexible tubing 52 which is positioned within a heating block 54. The coil 52 and tube 42 may comprise a single length of tubing with the coil formed at the distal end of the length of tubing 42. The length of tubing comprising the coil is selected to effectuate the desired degree of vaporization of moisture passing through the coil. Several factors influence the selection of this length including the temperature of the heating block, the distance separating the surface of the coil from the inside walls of the heater, the amount of moisture in the sample, the flow rate of gas through the coil, the wall thickness of the tubing and the total exposed surface area of the coil. The length of tubing comprising the coil segment may vary from 2 inches to 50 inches depending upon the specific application. In this embodiment, the length of the tubing section which comprises the coil 52 is approximately two feet.

The coil 52 is formed by wrapping the tubing 42 around a spool 56 having a head portion 58. As shown in FIG. 2, the head 58 has an aperture 60 formed in the center through which the tubing 42 is inserted. As best seen in FIG. 3, the spool 56 comprises two semi-circular wall sections 62,64. The semi-circular wall sections 62,64 of the spool 56 define two slots 66,68 which extend longitudinally along the length of the spool 56. The tubing 42 enters the interior region of the spool 56 through the aperture 60 in the head 58. The tubing 42 then exits the interior of the spool through one of the slots 66,68 and is wrapped around the exterior of the spool to form the coil 52. The end of the tubing then reenters the interior of the spool through one of the slots 66,68 and attaches to an input of a disc filter 70. In the embodiment shown in FIGS. 2, 4 and 5, the disc filter 70 also forms the base of the spool 56 opposite the head portion 58. In one embodiment, the diameter of the vaporization coil 52 is approximately 1.15 inches.

The heating block 54, shown in FIGS. 2, 3 and 5, comprises a main portion 72 and an extending portion 74 projecting therefrom. The main portion 72 has an cylindrical opening 76 suitably shaped and sized to accommodate the vaporization coil 52. The extending portion 74 has a channel 78 extending therethrough for receiving a heater 80. The heating block 54 may be fabricated from any suitable thermally conductive material such as aluminum or copper.

The cylindrical opening 76 has an interior wall 77 which completely surrounds the vaporization coil 52. This facilitates a uniform transfer of heat from the heating block 54 to the coil 52. When the coil 52 is inserted within the opening 76, the coil 52 is placed in close proximity to the interior wall 77 so as to allow effective heat transfer from the block 54 to the coils 52 so as to heat the gases flowing through the coil and vaporize any moisture contained therein. Typically, the outer exposed surface of the coil 52 is positioned such that the distance between the exposed surface of the coil and the wall 77 of the heater is in the range of from approximately 0.010 inches to approximately 0.100 inches.

The heater 80 may comprise an electrically resistive heating rod or other device capable of supplying heat to the block 54. The heater 80 raises the temperature of the block 54 to a predetermined temperature sufficient to vaporize moisture travelling through the coil 52. The heater 80 is regulated by a thermostat 82 mounted on the heater block 54 so that it senses the temperature of the block. The thermostat is selected to maintain the temperature of the block 54 at the predetermined temperature. One such thermostat which may be used is a bi-metallic switch which turns the heater on when the temperature of the block falls below a lower limit threshold and turns the heater off when the temperature of the block is above an upper limit threshold. The predetermined temperature of the block 54 is typically within the range of from approximately 37° C. to approximately 75° C. In one embodiment, the thermostat 82 has a control temperature of approximately 50° C.

The cylindrical opening 76 of the heater block 78 terminates in a smaller concentric opening 84 in which is positioned a female portion 85 of a two piece tubing connector. A male portion 86 of the two piece connector forms the output of the filter 70 which is connected to the output of the vaporization coil 52 and also forms the base of the vaporization coil. When the coil 52 is positioned within the opening 76 and the male and female connector portions 85,86 are joined together, the coil 52 is automatically aligned within the opening 76 of the heater block 54.

The filter 70 is disc-shaped and has a diameter in the range of from approximately 4 mm to approximately 50 mm. The filter 70 has a large surface area as compared to its volume and a small pore size. For example, the pore size may range from approximately 0.2 microns to approximately 1.2 microns. This configuration limits penetration of the filter by non-gaseous components present in the sample, such as particulates or liquids. These non-gaseous components are trapped at the surface of the filter. Thus, the filter 70 prevents secretions from the patient and other liquids from being delivered to the monitoring apparatus while allowing the gas sample to freely pass to the gas monitor. In view of its function, it is beneficial for the filter 70 to be constructed from hydrophobic filter materials, such as PTFE (Gortex) and hydrophobic grade acrylic copolymer membranes (Versapor). The disc filter 70 has an output which is connected to the input of the separator section 40.

The separator section 40 comprises a section of water vapor permeable tubing 88. Typically, the tubing 88 has a length in the range of from approximately 6 inches to approximately 48 inches, an inside diameter (ID) in the range of from approximately 0.020 inches to approximately 0.085 inches and a wall thickness in the range of from about 0.004 inches to about 0.008 inches. In one embodiment of the present invention, the tubing 88 comprises a polymer that is highly permeable to water vapor but has a very low permeability for the respiratory and anesthetic gases being analyzed. Thus, water vapor rapidly diffuses out of the gas sample when the sample passes through the separator section 40. One commercially available product having these characteristics is a polymer which was developed by Du Pont scientists and is marketed in tubing form as Nafion ® tubing. Nafion ® is a perfluorinated ion-exchange membrane prepared from polytetrafluoroethylene and perfluorinated monomers containing sulfonic acid group, of the following general structure:

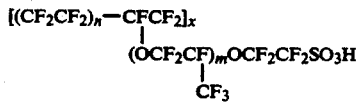

Nafion ® is made by reacting Tetrafluoroethylene (Teflon ®) and Perfluoro-3,6 Dioxa-4 Methyl-7 Octensulfonic Acid. Perma Pure Products Inc. of Toms River, N.J., produces tubing from the thermoplastic polymer of the Nafion ® material. After extrusion, the thermoplastic form is converted through a series of chemical reactions into the final acid form which has a high capacity for absorbing and desorbing water. In general, the molecular structure of Nafion ® tubing is:

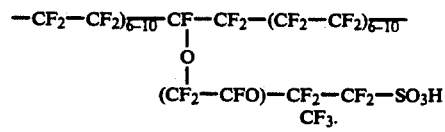

In one embodiment, a section of Nafion ® tubing having a length of approximately 24 inches, an ID of approximately 0.040 inches and a wall thickness of approximately 0.006 inches is used. The Nafion ® tubing 88 is attached directly to the outflow side of the disc membrane filter 70, thus allowing a majority of the water vapor contained in the sample and vaporized in the vaporization coil 52 to diffuse out of the gas transport system through the Nafion ® tubing before the sample reaches the gas analysis cell. The output end of the tubing 88 is attached to the connector 47 which connects to the gas analysis cell. In the configuration shown, the Nafion ® tubing 88 is near the end of the gas transport system and thus can be permanently attached to the gas analyzer at its input. In this position, the Nafion ® tubing 88 does not require cleaning and sterilization after each patient use.

The system and processes described herein were developed primarily for use in preventing water contamination during the analysis of respiratory gases. However, the invention may also be useful for other devices and applications. While the above description comprises an embodiment of the invention as applied to the analysis of respiratory gases there are other applications which will be obvious to those skilled in the art.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. An apparatus for sampling respiratory gases of a patient and delivering same to a gas analysis cell comprising:
   a patient link section having a patient link input end and a patient link output end, said patient link input end having means to receive a sample of respiratory gases;
   a vaporization section means for vaporizing moisture contained in said sample of respiratory gases, said vaporization section means having a vaporization input end and a vaporization output end, said vaporization input end connected to said patient link output end, said vaporization input end having means to receive said sample of respiratory gases from said patient link section, said vaporization section means further comprising:
   a vaporization coil having a coil input, a plurality of proximate turns, and a coil output, wherein said coil input connects to said vaporization input end;
   a membrane filter having a filter input and a filter output, wherein said filter input connects to said coil output and said filter output connects to said vaporization output end; and a heated block having a means for heating said block to a predetermined temperature, said heated block defining a chamber within said block, said vaporization coil positioned within said chamber; and a separator section means having a separator input and a separator output, said separator input connected to said vaporization output end and said separator output having means for delivering said sample to a gas-analysis cell, wherein said separator section means is for receiving said sample and vaporized moisture therein from said vaporization output end, and removing said vaporized moisture from said sample of respiratory gases.

2. An apparatus as defined in claim 1, wherein said means for heating comprises an electrically resistive heating element, said electrically resistive heating element coupled to a thermostat, said thermostat controlling the temperature of said heated block.

3. An apparatus as defined in claim 1, wherein said separator section means further comprises a water vapor permeable section positioned intermediate said separator input and output.

4. An apparatus as defined in claim 3 wherein said water vapor permeable section comprises a section of tubing made from a perfluorinated ion-exchange membrane prepared from polytetrafluoroethylene and perfluorinated monomers containing sulfonic acid groups, of the following general structure:

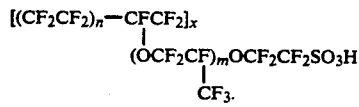

5. A gas drying apparatus comprising:

a first portion, wherein said first portion further comprises:

a patient link having a patient link input end and a patient link output end, said patient link input end having means to receive a sample of gases from a patient;

a vaporization section means for vaporizing moisture contained in said sample of gases, said vaporization section means having a vaporization section input and a vaporization section output, said vaporization section input coupled to said patient link output end, said vaporization section means having means to receive said sample from said patient link and to vaporize moisture contained in said sample of gases; and a filter means for removing nongaseous components in said sample of gases, said filter means having a filter input and a filter output, said filter input coupled to said vaporization section output to receive said sample of gases from said vaporization section means; and a second portion wherein said second portion further comprises:

a heating section means for heating said vaporization section means; and a water vapor permeable section having an input end and an output end wherein said water vapor permeable section input end is coupled to said filter output to receive said sample of gases from said filter means, said water vapor permeable section having means to expel said vaporized moisture between said water vapor permeable section input end and said water vapor permeable section output end as said sample of gases traverses said water vapor permeable section such that said sample of gases which exits said water vapor permeable section output end contains less vaporized moisture than when it entered said water vapor permeable section input end.

6. An apparatus as defined in claim 5, wherein said water vapor permeable section comprises a section of tubing made from a perfluorinated ion-exchange membrane prepared from polytetrafluoroethylene and perfluorinated monomers containing sulfonic acid groups, of the following general structure:

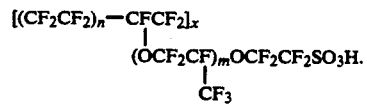

7. An apparatus as defined in claim 5, wherein said first portion is formed of disposable materials.

8. An apparatus as defined in claim 5, wherein said heating section means further comprises:

a thermally conductive block; and an electrical heating element, said electrical heating element coupled to said conductive block, said heating element having means to maintain the temperature of said block at a predetermined temperature.

* * * * *